US00PP20501P2

(12) United States Plant Patent
Dekker

(10) Patent No.: US PP20,501 P2
(45) Date of Patent: Nov. 24, 2009

(54) ***EUPHORBIA* PLANT NAMED 'PP0006'**

(50) Latin Name: *Euphorbia milii*
Varietal Denomination: PP0006

(76) Inventor: Adrianus Dekker, Langedijker 9, Warmenhuizen HJ (NL) 1749HJ ( * ) Notice: Subject to any disclaimer, the term of this patent is extended or adjusted under 35 U.S.C. 154(b) by 0 days.

(21) Appl. No.: 12/157,171

(22) Filed: Jun. 6, 2008

(51) Int. Cl.
*A01H 5/00* (2006.01)

(52) U.S. Cl. ..... Plt./302

(58) Field of Classification Search ..... Plt./302
See application file for complete search history.

(56) References Cited

OTHER PUBLICATIONS

Upov Plant Variety Database 2008/04 search for cultivar PP0006.*

* cited by examiner

*Primary Examiner*—Annette H Para

(57) ABSTRACT

A new and distinct *Euphorbia milii* cultivar named 'PP0006' is disclosed, characterized by mainly pink flowers. The cultivar is commercially important as it flowers richly during cold, dark winter conditions. The new variety is a *Euphorbia milii*, and naturally blooms continuously.

1 Drawing Sheet

Figure 1:
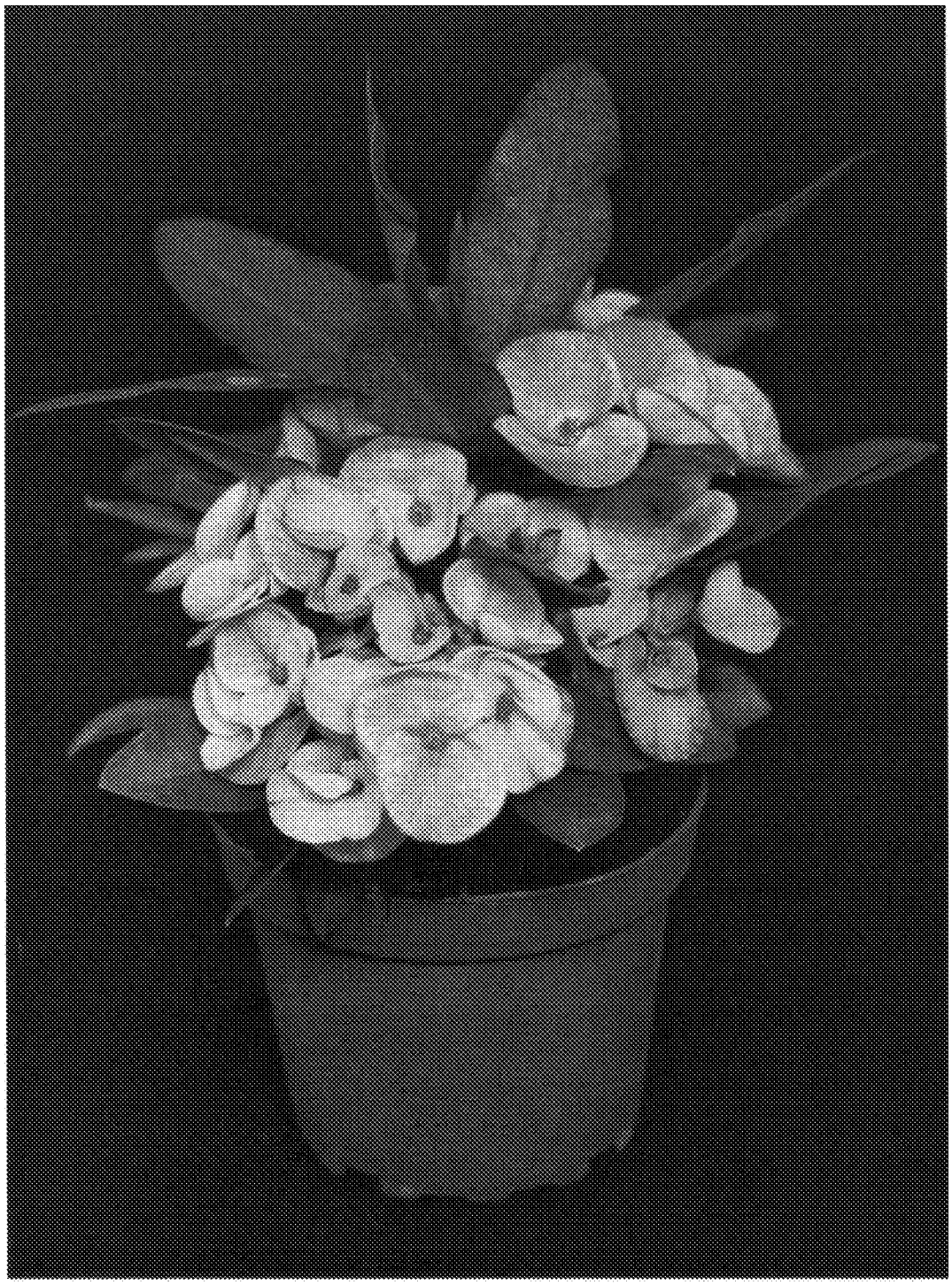

Latin name of the genus and species: *Euphorbia milii.*
Variety denomination: 'PP0006'.

BACKGROUND OF THE INVENTION

The new cultivar is the product of a planned breeding program under the direction of the inventor, Adrianus Cornelis Dekker, a citizen of Holland. The objective of the breeding program was to produce plants of *Euphorbia milii* with better flowering under low light and cold temperature conditions. The seed parent is the unpatented, proprietary seedling variety referred to as *Euphorbia milii* 'PP0087.' The pollen parent is the unpatented, proprietary seedling variety referred to as *Euphorbia milii* 'PP0093.' The new variety was discovered January 2005 by the inventor in a group of seedlings resulting from that crossing, in Monster, Holland.

Asexual reproduction of the new cultivar 'PP0006' by vegetative cuttings was performed in Monster, Holland, in February 2005 and has shown that the unique features of this cultivar are stable and reproduced true to type in successive generations.

SUMMARY OF THE INVENTION

The cultivar 'PP0006' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'PP0006' These characteristics in combination distinguish 'PP0006' as a new and distinct *Euphorbia milii* cultivar:

1. Rich flowering under dark, cold conditions.
2. Bright green foliage.
3. Unique pink and white flower coloration.

PARENT COMPARISON

Plants of the new cultivar 'PP0006' are similar to plants of the seed parent, *Euphorbia milii* 'PP0087' in most horticultural characteristics, however, plants of the new cultivar 'PP0006' produce more flowers.

Plants of the new cultivar 'PP0006' are similar to plants of the pollen parent, *Euphorbia milii* 'PP0093' in most horticultural characteristics, however, plants of the new cultivar 'PP0006' have pink flowers with some white coloration, whereas the pollen parent has entirely white flowers.

Plants of the new cultivar 'PP0006' are similar to plants of the commercial variety, *Euphorbia milii* 'Pandora,' unpatented, in most horticultural characteristics. However, plants of the new cultivar 'PP0006' differ in the following characteristics;

1. 'PP0006' produces more flowers under cold, dark conditions.
2. 'PP0006' produces a darker flower, especially under winter conditions.
3. 'PP0006' produces a larger diameter flower.

BRIEF DESCRIPTION OF THE PHOTOGRAPH

The accompanying photograph in FIG. 1 illustrates in full color a typical plant of 'PP0006' grown in a greenhouse. The pot size is a commercial 15 cm container, approximately. The plant shown is approximately 15 weeks old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'PP0006' plants grown in a commercial greenhouse in Monster, The Netherlands from March 2007 to June 2007. The growing temperature ranged from approximately 21° C. at night to 23° C. during the day. Measurements and numerical values represent averages of typical flowering types. No chemical or photoperiodic treatments were given.
Botanical classification: *Euphorbia milii* cultivar 'PP0006.'

PROPAGATION

Time to rooting: 10 to 14 days at approximately 18° C.
Root description: Fine, fibrous.

PLANT

Growth habit: Upright tender perennial, suitable for indoor ornamental use
Height: Approximately 29.8 cm.
Plant spread: Approximately 37.7 cm.
Growth rate: Moderate.
Branching characteristics: Weak branching, characteristic of species.
Length of lateral branches: Approximately 7.1 cm.
Diameter of lateral branches: Approximately 1.2 cm.
Quantity of lateral branches: Approximately 3 primary lateral branches.
Texture of lateral branches: 5-angled, otherwise smooth.
Color of lateral branches: Near RHS Green 143A.
Aspect: Upright.
Number of leaves per lateral branch: Approximately 6.
Age of plant described: Approximately 15 weeks from a rooted cutting.

FOLIAGE

Leaf:
*Arrangement.*—Alternate, simple.
*Average length.*—Approximately 14.0 cm.
*Average width.*—Approximately 3.8 cm.
*Shape of blade.*—Oblanceolate.
*Apex.*—Acute to abruptly acute.
*Base.*—Cuneate.
*Attachment.*—Sessile.
*Margin.*—Entire.
*Texture of top surface.*—Smooth.
*Texture of bottom surface.*—Smooth.
*Leaf internode length.*—Approximately 0.7 cm.
*Color.*—Young foliage upper side: Near R.H.S. Green 143A. Young foliage under side: Between RHS Green 143C and Yellow-Green144A. Mature foliage upper side: Near RHS Green 137A. Mature foliage under side: Near RHS Yellow-Green 146B.
*Venation.*—Type: Pinnate Venation color upper side: Near RHS Green 137B. Venation color under side: Near RHS Yellow-Green 146B.
Petiole: Not present.
Other characteristics: One large and two smaller thorns are placed on each side of each leaf, average length of the primary thorn: 1.6 cm, average length of secondary thorns: 0.7 cm, average width of primary thorn at base: 4 mm, average width of secondary thorns at base: 2 mm, thorns pointed outward, colored near RHS Greyed-Orange 166B, base colored near RHS Green 143A.

FLOWER

Bloom period: Year-round, continuous.
Bud:
*Bud shape.*—Spherical.
*Bud length.*—Approximately 0.1 cm.
*Bud diameter.*—Approximately 0.1 cm.
*Bud color.*—Near Yellow-Green 145A/B.
*Rate of opening.*—Approximately 3 days from bud stage to open flower.
Inflorescence:
*Form.*—Axillary, compound cyme.
*Diameter of entire inflorescence.*—Approximately 15.8 cm.
*Depth of entire inflorescence.*—Approximately 13.6 cm.
*Quantity of individual flowers in inflorescence.*—Avg. 9.
Individual flowers:
*Form.*—Staminate flowers consisting of anthers only, no petals, no sepals, each "flower" is supported by one conspicuous gland. Individual (staminate) flowers are grouped in five, supported by two conspicuous bracts.
*Quantity per plant.*—Avg. 126. Approximately 50% open at one time.
*Length.*—Approximately 0.15 cm.
*Width.*—Approximately 0.2 cm.
*Aspect.*—Upright to outward.
*Duration on plant.*—Approximately 1 week. Self-cleaning.
Fragrance: None.
Glands: Each individual staminate flower is supported by one gland.
*Shape.*—Kidney-shaped.
*Length.*—2 mm, average
*Width.*—4 mm.
*Color.*—Near RHS Orange N25A.
Other floral characteristics: Flowers are grouped in five, supported by two conspicuous bracts,
Bracts:
*Shape.*—Orbicular to reniform.
*Apex.*—Top rounded to very short abruptly acute.
*Base.*—Reniform.
*Length.*—2.8 cm, average.
*Width.*—3.5 cm.
*Texture.*—Matte.
*Color.*—Upper side of immature bract: Near RHS Red 52B. Under side of immature bract Near RHS Red 56B. Upper side of mature bract: Near RHS Red 52A. Under side of mature bract: Near RHS 56B, darker towards the margins; 55C.
Peduncle:
Peduncle length: Approximately 12.3.
Peduncle diamter: Approximately 0.4 cm.
Color: Near RHS Yellow-Green 144A.

REPRODUCTIVE ORGANS

Androecium:
*Stamens.*—1, branched and holding 4 anthers.
*Anther length.*—Approximately 0.05 cm.
*Anther color.*—Near Red; 46A, but darker. Filament colored red 51A.
*Pollen color.*—Near Yellow 13C.
*Pollen quantity.*—Low.
Gynoecium: Not present.

OTHER CHARACTERISTICS

Disease resistance: Neither resistance nor susceptibility to diseases or pests has been observed in this variety.
Drought tolerance and cold tolerance: Tender perennial. Tolerates high temperature to at least 40° C. No drought tolerance or cold has been observed.
Fruit/seed production: Fruits and seeds are not produced.

What is claimed is:

1. A new and distinct cultivar of *Euphorbia* plant named 'PP0006' as herein illustrated and described.

* * * * *